United States Patent [19]

Kobayashi

[11] Patent Number: 4,740,071

[45] Date of Patent: Apr. 26, 1988

[54] SUBJECTIVE OPHTHALMIC INSTRUMENT

[75] Inventor: Katsuhiko Kobayashi, Tokyo, Japan

[73] Assignee: Tokyo Kogaku Kikai Kabushiki Kaisha, Tokyo, Japan

[21] Appl. No.: 784,326

[22] Filed: Oct. 2, 1985

[30] Foreign Application Priority Data

Oct. 2, 1984 [JP] Japan .................. 59-206775

[51] Int. Cl.$^4$ .................. A61B 3/10; A61B 3/14
[52] U.S. Cl. .................. 351/206; 351/211
[58] Field of Search .............. 351/206, 207, 208, 243, 351/211; 354/62

[56] References Cited

U.S. PATENT DOCUMENTS 4,279,478 7/1981 Matsumura .................. 351/206

4,283,126 8/1981 Reiner .................. 351/243 X

*Primary Examiner*—Rodney B. Bovernick
*Attorney, Agent, or Firm*—Brumbaugh, Graves, Donohue & Raymond

[57] ABSTRACT

A subjective ophthalmic instrument has optotypes which are observed by the patient through a correcting lens system of adjustable refractive power. The subjective ophthalmic instrument further has a optotype examination system which includes an imaging optical system for producing an image of a patient's fundus projected with an image of the optotypes at a camera tube, and display means for displaying the optotype image in accordance with the output of the camera tube.

4 Claims, 3 Drawing Sheets

SUBJECTIVE OPHTHALMIC INSTRUMENT

BACKGROUND OF THE INVENTION

1. Field of the Invention

The present invention relates to a subjective ophthalmic instrument for examining eyes. More specifically, the present invention pertains to a subjective ophthalmic instrument by which the operator can observe an image of optotypes formed on the patient's fundus in order to examine the eye refractive power, the eye optical system and the optic nerve of the patient.

2. Description of the Prior Art

Conventionally, ophthalmic instruments are divided into two types, namely, objective ophthalmic instruments and subjective ophthalmic instruments. In an objective ophthalmic instrument, an image of a split mark such as a split slit is projected on the patient's fundus so that the refractive power of the patient's eye is measured in accordance with amount of image splitting. In a subjective ophthalmic instrument, the patient watches optotypes such as a Landholt ring through a correcting lens system, which is adjusted in accordance with the patient's response so that the patient can see the optotypes clearly. The patient's refractive power is measured in terms of the amount of adjustment.

The objective ophthalmic instrument has an advantage in that the patient's response is not necessary, while the subjective ophthalmic instrument has an advantage in being able to directly measure patient's precise refractive power. With the subjective ophthalmic instrument, however, the operator cannot examine how the image of the optotypes are produced on the patient's fundus so that the measurement is performed through the response of the patient. Since the patient's response sometimes includes errors, quick and precise examination of the eye cannot be expected with the subjective ophthalmic instrument.

Furthermore, in the subjective ophthalmic instrument, when the image of the optotypes formed at the fundus is examined while the patient watches the image of optotypes the operator cannot watch the image of the optotypes precisely, because the image is blurred because of the low reflection efficiency of the fundus and low conversion efficiency of the photo-electric element used.

In view of the frequent incorrectness of the patient's response, it has become common to carry out refractive power measurement by a rough measurement using an objective ophthalmic instrument and subsequently referring to the rough refractive power data in carrying out a precise measurement using a subjective ophthalmic instrument provided in the same objective ophthalmic instrument or independently of it.

In the conventional subjective ophthalmic instrument, when the patient cannot see the optotypes clearly at any adjustment of the correcting lens system, the operator cannot judge whether the patient's eye suffers from a disease affecting his eye optical system between the cornea and the retina or a disease affecting his optic nerve extending to the retina.

DESCRIPTION OF THE INVENTION

Object of the Invention

It is an object of the present invention to provide a subjective ophthalmic instrument in which the operator can observe how an image of a optotypes is produced on a patient's fundus.

Another object of the present invention is to provide a subjective ophthalmic instrument in which the operator can observe a display showing an image of the optotypes extracted from an image of the patient's fundus, whereby he is able to examine the focusing state of the image of the optotypes precisely and quickly.

A further object of the present invention is to provide a subjective ophthalmic instrument by which the operator can judge whether the patient's eye suffers from a disease in his eye optical system between the cornea and the retina or from a disease in his optic nerve, when the patient cannot see the optotypes clearly at any adjustment of the correcting lens system therein.

DESCRIPTION OF THE INVENTION

According to the present invention, the above and other objects can be accomplished by a subjective ophthalmic instrument wherein a patient is caused to watch optotypes through a correcting lens system of adjustable refraction, characterized by having optotypes examination system which includes an imaging optical system for producing an image of a patient's fundus projected with an image of the optotypes at a camera tube, and display means for displaying the optotypes image in accordance with the output of the camera tube.

According to a specific aspect of the present invention, there is provided a subjective ophthalmic instrument in which the optotypes examination system further includes a picture processing system for removing picture signal corresponding to the fundus from the output of the camera tube so as to extract a picture signal of the image of the optotypes.

According to another specific aspect of the present invention, the point picture intensity distribution is of a transference function of a normal eye or an eye having an abnormal optic nerve.

DESCRIPTION OF THE PREFERRED EMBODIMENTS

Figure 1:
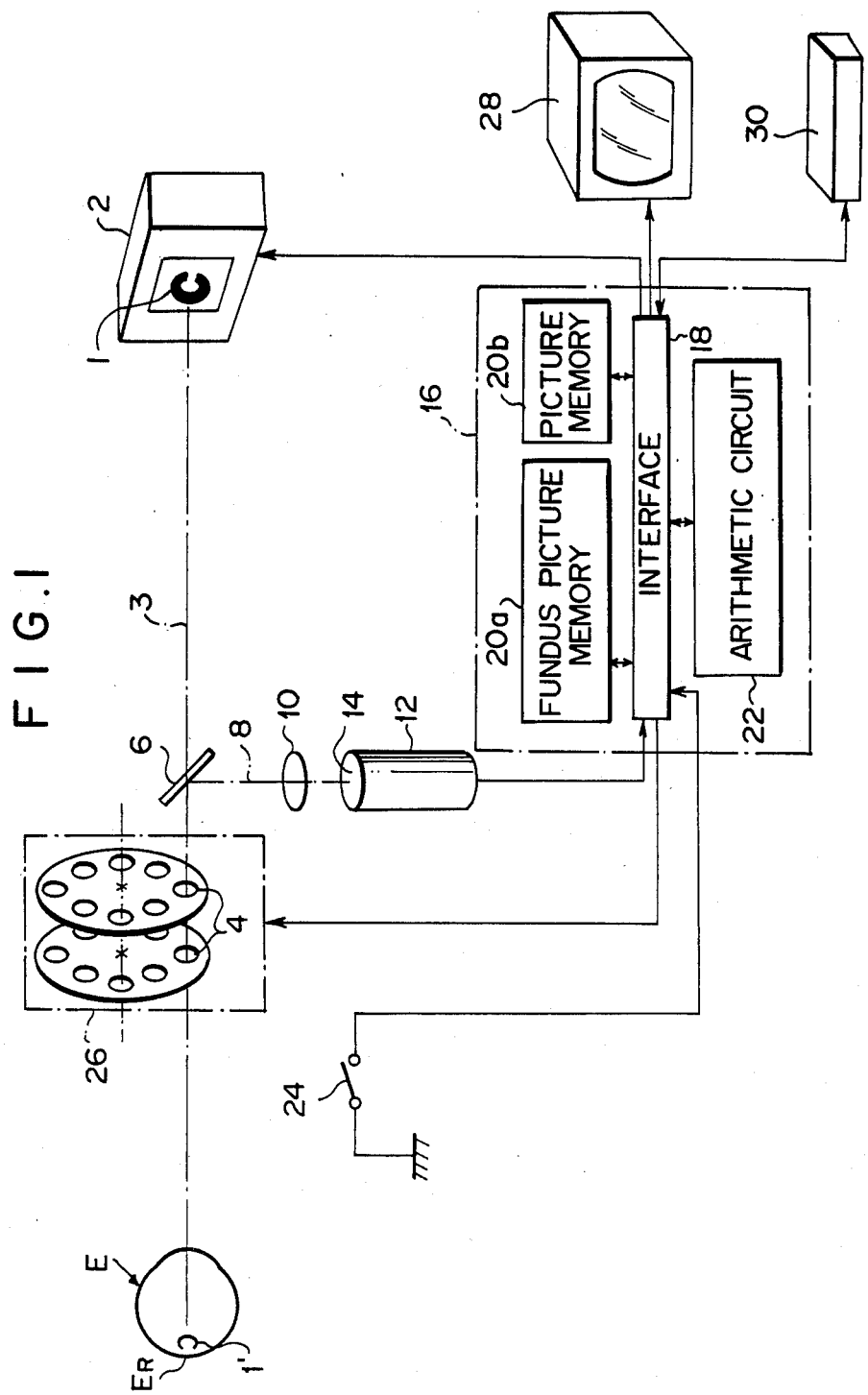
FIG. 1 is an explanatory view for explaining a subjective ophthalmic instrument in accordance with one embodiment of the present invention.

Referring now to the drawings, there is shown a subjective ophthalmic instrument in which the present invention is embodied. The subjective ophthalmic instrument shown in FIG. 1 includes display means 2 operated by an operator for forming an image 1' of optotypes 1 on the patient's fundus $E_R$, correcting lens means 4 located on an optical axis 3 of the display means 2 for correcting the refractive power of the patient's eye E so that the patient can see the optotypes 1 through the correcting lens means 4. In other words, the image 1' of the optotypes 1 is produced on the fundus $E_R$.

There is obliquely provided a half-mirror 6 on the optical axis 3 between the display means 2 and the correcting lens means 4. On an imaging axis 8, which is an optical axis reflected at the half mirror 6, there are provided an objective lens 10 and a camera tube 12 so that the fundus $E_R$ is located in conjugate with the photo-electric plane 14 of the camera tube 12 with respect to the objective 10.

The camera tube 12 is connected with an interface 18 in a picture signal processing unit 16 and receives the output of the camera tube 12. The picture signal processing unit 16 comprises the interface 18, a fundus picture memory 20a and a picture memory 20 both connected with the interface 18, and an arithmetic circuit 22. The fundus picture memory 20a is adapted to memorize the picture signal of the patient's fundus $E_R$ uniformly illuminated before he sees the optotypes 1. The image memory 20b is adapted to memorize the picture signal of the patient's fundus $E_R$ formed with an image of the optotypes 1 when he sees the optotypes 1. The arithmetic circuit 22 is adapted to process picture signals of the patient's fundus $E_R$ in a manner as described hereinafter.

Figure 2:
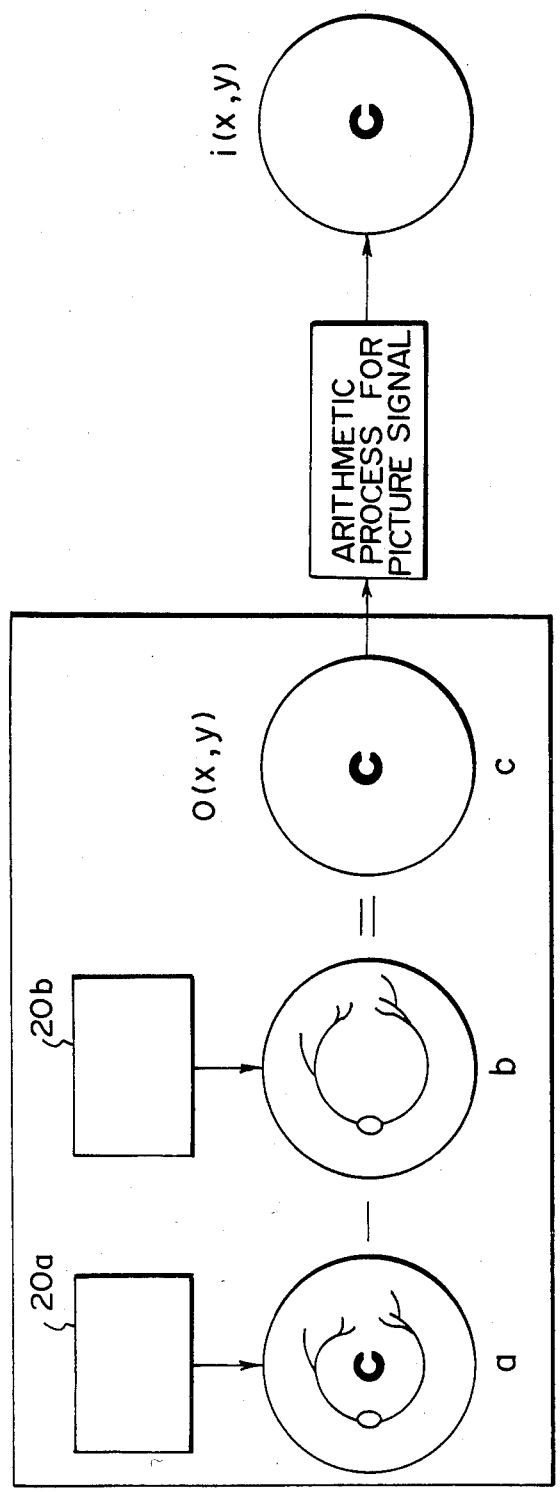
FIG. 2 is an explanatory view for explaining the principle of a picture processing system.
Figure 3:
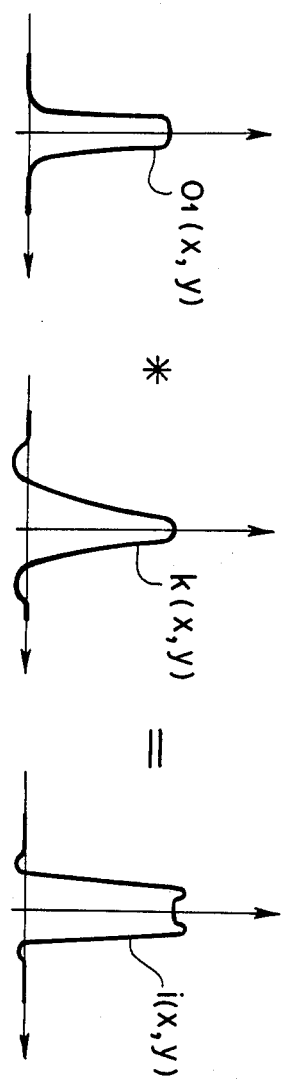
FIG. 3 is an explanatory graphical representation for explaining the principle of a picture processing system.

In a first processing step of the arithmetic circuit 22, as shown in FIG. 2, a first fundus picture signal b of the fundus image not including the optotypes image 1' is removed from a second fundus picture signal a of the fundus image including the optotype image 1', so that the picture signal of the focusing mark image o(x,y) is extracted. If the brightness of the fundus image at the time the patient sees the optotypes 1 differs from the brightness at the time of uniform illumination, this suggests that the first fundus picture signal b is multiplied depending upon the difference between the above-mentioned brightnesses.

In a second processing step of the arithmetic circuit 22, the picture signal o(x,y) is convoluted by point image intensity distribution of a normal optic nerve k(x,y). Namely, it is known that a person does not directly perceive the image formed on the retina, but perceives the image after image signal processing, such as processing for enhancing the image profile or for strengthening light having a specific wavelength. In other words, the image formed on the retina does not produce the vision directly, but, when the image having a brightness distribution $O_1(x,y)$ is produced at the retina, the person's vision is affected by the point image intensity distribution k(x,y) of the optic nerve as follows, $$i(x,y) = O_1(x,y) * k(x,y)$$

(*: convolution)
As a result, the person can see the object whose image has the brightness distribution i(x,y).

In the ophthalmic instrument, there are provided a patient response switch 24, by which the patient inputs his answers in response to presented optotypes 1, a correcting lens adjusting system 26 for adjusting the correcting lens means 4, a monitor TV 28 for allowing the operator to observe the image of the optotypes 1, and a control panel 30, through which the operator controls the ophthalmic instrument. The switch 24, the correcting lens adjusting system 26, the monitor TV 28, and the control panel 30 are connected with the interface 18.

Now, measurement using the above-mentioned subjective ophthalmic instrument will be explained. In the first step, the fundus $E_R$ is uniformly illuminated by the display means 2 which has a bright screen without any image of optotypes 1 or by fundus illuminating means (not shown in the Figures). In the second step, the adjusting system 26 is controlled through the control panel 30 and the image of the fundus $E_R$ is produced at the photo-electric plane 14 of the camera tube 12. The picture signal of the fundus $E_R$ with no optotype image 1' formed therein is supplied to the fundus picture memory 20a through the interface 18 and memorized therein.

In the third step, the operator controls the control panel 30 so that the optotypes 1 are displayed on the display means 2 and has the patient look at the optotypes 1. At this stage, it is possible that the optotype image 1' is not focused on the fundus $E_R$. The picture signal of the fundus $E_R$ having the optotype image 1' is supplied to the process unit 16 so that picture signal of the optotype image 1' is extracted therefrom. The picture signal as extracted in the above-mentioned manner is applied to the monitor TV 28 which displays the optotype image 1' thereon. Watching the focusing mark image 1' on the monitor TV 28, the operator adjusts the adjusting system 26 through the control panel 30 so that the optotype image 1' is precisely focused on the fundus $E_R$. The refractive power of the eye E is calculated in accordance with correction amount of the adjust system 26. If the patient cannot see the optotypes 1 in the best condition even though the image 1' on the monitor TV 28 shows that the image 1' is distinctly formed on the fundus, it is judged that the patient's optic nerve is not normal.

The point image intensity distribution k(x,y) of the optic nerve system cannot be obtained directly by experiment. However, the point image intensity distribution j(x,y) of the eye optical system can be measured objectively, and the brightness distribution (j(x,y) * k(x,y)) can be measured psychophysically. Therefore, the intensity distribution k(x,y) can be calculated from data obtained by the objective and psychophysical measurements.

Though, in the above-mentioned embodiment the operator controls the control panel 30 during the subjective measurement, the measurement in accordance with the present invention can be automatically carried out by inputting the steps of the subjective measurement to the arithmetic circuit 22.

Furthermore, in the embodiment the image signal o(x,y) is convoluted by the point image intensity distribution k(x,y) of the normal optic nerve. However, if the image signal o(x,y) is convoluted by the point image intensity distribution which is expected to appear for a predetermined abnormal optic nerve, it is possible to learn how the patient having the predetermined abnormal optic nerve sees the object.

The invention has thus been shown and described with reference to a specific embodiment, however, it should be noted that the invention is in no way limited to the details of the illustrated arrangements but changes and modifications may be made without departing from the scope of the appended claims.

What is claimed is:

1. A subjective opthalmic instrument for measuring the refractive power of a patient's eye wherein a patient is caused to view optotypes through a correcting lens system of adjustable refractive power characterized by having an optotype examination system which includes a camera tube, an imaging optical system for producing an image of the patient's fundus projected with an image of said optotypes onto said camera tube, a picture processing system for removing from the output of said camera tube picture information corresponding to the fundus so as to extract a picture signal of the image of said optotypes, and display means coupled to said picture processing system for displaying the image of the optotype in accordance with the output of said camera tube.

2. A subjective opthalmic instrument in accordance with claim 1 in which said picture processing system includes means for convoluting the picture signal of the image of said optotypes with a point picture intensity distribution.

3. A subjective opthalmic instrument in accordance with claim 3 wherein the point picture intensity distribution is in accordance with a transference function of a normal eye.

4. A subjective opthalmic instrument in accordance with claim 3 wherein the point picture intensity distribution is in accordance with a transference function of an eye having an abnormal optic nerve.

* * * * *